US 6,592,813 B1
United States Patent
Fox et al.
(45) Date of Patent: Jul. 15, 2003

(54) MALODOUR COUNTERACTING TREATMENT

(75) Inventors: Rodney Thomas Fox, Cottingham (GB); Neale Harrison, Staffordshire (GB); John Farrell Hughes, Southampton (GB); Duncan Roger Harper, Hull (GB); Lindsey Faye Whitmore, Winchester (GB)

(73) Assignees: University of Southampton, Southampton (GB); Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 09/720,898

(22) PCT Filed: Jun. 23, 1999

(86) PCT No.: PCT/GB99/01978

§ 371 (c)(1),
(2), (4) Date: Jun. 11, 2001

(87) PCT Pub. No.: WO00/01421

PCT Pub. Date: Jan. 13, 2000

(30) Foreign Application Priority Data

Jul. 2, 1998 (GB) .............................................. 9814366

(51) Int. Cl.$^7$ .............................. A61L 9/00; A61L 9/04; A62B 7/08; A01G 23/10; A62C 5/02

(52) U.S. Cl. ................................. 422/5; 422/1; 422/28; 422/33; 422/123; 239/3; 239/8; 239/337; 239/690; 239/708; 424/45; 424/76.6; 424/78; 424/83

(58) Field of Search .............................. 422/1, 5, 28–30, 422/33, 120, 292, 297–299, 300, 305–306; 239/3, 8, 690, 337, 708; 424/83, 78, 45, 76.6

(56) References Cited

U.S. PATENT DOCUMENTS

| 4,740,366 A | * | 4/1988 | Winston et al. |
| 5,085,849 A | * | 2/1992 | Sampson et al. |
| 5,679,324 A | | 10/1997 | Lisboa et al. .................. 424/45 |

FOREIGN PATENT DOCUMENTS

| BE | 827298 | 7/1975 |
| JP | 2-069407 | 3/1990 |
| JP | 3-052805 | 3/1991 |
| JP | 3-284616 | 12/1991 |
| SU | 544433 | 2/1977 |
| WO | WO 96/28033 | 9/1996 |
| WO | WO 97/28883 | * 8/1997 |
| WO | WO 98/24356 | * 6/1998 |

* cited by examiner

*Primary Examiner*—Robert J. Warden, Sr.
*Assistant Examiner*—Monzer R. Chorbaji
(74) *Attorney, Agent, or Firm*—Fish & Richardson P.C.

(57) ABSTRACT

An improved method of counteracting or neutralizing airborne malodour comprising directing at the source of the malodour liquid droplets from a spray device containing a malodour counteracting composition, the improved method comprising imparting a unipolar charge to the said liquid droplets by double layer charging during the spraying of the liquid droplets by the spray device, the unipolar charge being at a level such that the said droplets have a charge to mass ratio of at least $\pm 1 \times 10^{-4}$ C/kg.

14 Claims, 3 Drawing Sheets

L = 6.7332
a = .4992

MALODOUR COUNTERACTING TREATMENT

BACKGROUND OF THE INVENTION

The present invention relates to the treatment of malodours, in particular, airborne malodours which may be caused or carried by airborne particles or by entities in a gaseous state.

A known method of counteracting or neutralising a malodour involves the use of an aerosol spray device containing a composition comprising one or more malodour counteractants and which, when activated, produces an aerosol spray which may be targeted at the source of the malodour. Various known products are marketed for this purpose.

Where the malodour is caused wholly or partly by airborne particles, a low collision rate between the malodour counteractant and the malodour particle occurs using known aerosol spray devices and so results in an inefficient malodour counteracting process. The practical consequence of this inefficiency is that the malodour counteractant, which may be or may include a malodour masking ingredient, has to be used in large amounts in order to achieve the desired effect. This in turn leads to unwanted side effects, such as a strong perfume smell or a limited fragrance choice.

Even when the malodour is caused wholly or partly by a non-particulate airborne source, the use of the known aerosol spray devices containing malodour counteracting compositions is still rather inefficient. In order to deliver an aerosol spray which can be projected over a reasonable distance, the design of the device, and in particular, the design of the spray head of the device, results in the emission of a spray with a small spread angle. Thus, most of the spray travels at least initially along or close to a central spray line extending from the spray head. Accordingly, if the source of the malodour spreads out to a significant extent spatially in directions lateral to the line of spray, it is necessary to deliver a large amount of the aerosol spray in order effectively to dispose of the malodour. Thus, to remove a malodour from a room, a considerable amount of aerosol spray would be required to be delivered throughout the room space.

We have now developed an improved method of counteracting or neutralising an airborne malodour.

SUMMARY OF THE INVENTION

Accordingly, the present invention provides a method of counteracting or neutralising airborne malodour comprising directing at the source of the malodour liquid droplets from a spray device containing a malodour counteracting composition the method comprising imparting a unipolar charge to the said liquid droplets by double layer charging during the spraying of the liquid droplets by the spray device, the unipolar charge being at a level such that the said droplets have a charge to mass ratio of at least $+/-1\times10^{-4}$ C/kg.

DETAILED DISCLOSURE

Figure 1:
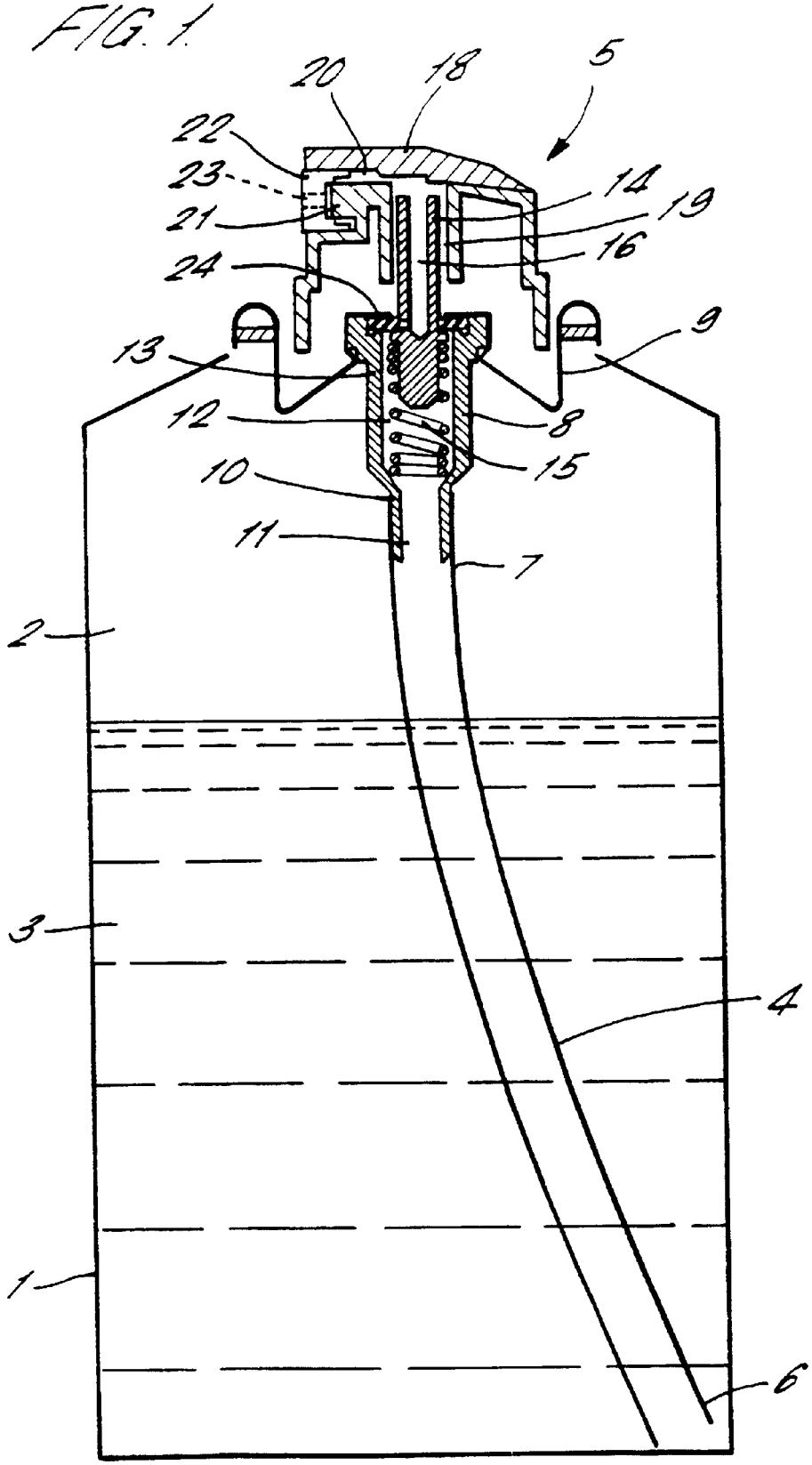
FIG. 1 is a diagrammatic cross section through an aerosol spraying apparatus in accordance with the invention.

The method of the present invention enables an airborne malodour, for example in a room or other enclosed space, to be treated effectively whether the cause of the malodour is of particulate origin, such as smoke, or gaseous origin, such as cooking odours, or finely dispersed liquid droplets, or resinous material. The method of the present invention is extremely effective in counteracting or neutralising malodours since the charged aerosol spray droplets have a greater collision rate with malodorous particles contained in the air. Furthermore, since the charged droplets carry the same polarity of charge on spraying from a spray device they repel one another and thus spread out more from the central spray line than they would if not charged in accordance with the invention. Thus, the spray covers a greater volume of air space, than a conventional air spray, enabling a more effective treatment to be obtained for a lesser volume of spray than with a conventional spray device.

It is preferred that the unipolar charge which is imparted to the liquid droplets is generated solely by the interaction between the liquid within the spray device and the spray device itself as the liquid is sprayed therefrom. In particular, it is preferred that the manner in which a unipolar charge is imparted to the liquid droplets does not rely even partly on the connection of the spray device to any external charge inducing device, such as a source of relatively high voltage, or any internal charge inducing device, such as a battery. With such an arrangement, the spray device is entirely self-contained, making it suitable for use both in industrial, institutional and domestic situations.

Preferably, the spray device is a domestic pressure-spraying device devoid of any electrical circuitry but which is capable of being hand held.

Typically such a device has a capacity in the range of from 10 ml to 2000 ml and can be actuated by hand, or by an automatic actuating mechanism. A particularly preferred domestic device is a hand-held aerosol can.

Preferably, therefore the droplet charge to mass ratio of at least $+/-1\times10^{-4}$ C/kg is imparted to the liquid droplets as a result of the use of an aerosol spray device with at least one of the features of the material of the actuator, the size and shape of the orifice of the actuator, the diameter of the dip tube, the characteristics of the valve and the formulation of the malodour counteracting composition contained within the aerosol device being chosen in order to achieve the said droplet charge to mass ratio by double layer charging imparting the unipolar charge to the droplets during the actual spraying of the liquid droplets from the orifice of the aerosol spray device.

As a result of the method of the present invention, a counteraction of the malodour is perceived with the use of much less malodour counteractant composition than has previously been achieved. Furthermore, in view of the increased collision rate between the malodour counteractant and airborne particles and the increased spread of the aerosol spray for a given amount of liquid sprayed from the aerosol the efficiency of malodour counteraction is increased.

These results are achieved because of the high unipolar charge imparted to the liquid droplets of the aerosol spray. The individual droplets carry the same polarity charge and thus target the malodour particles having the opposite charge or which are electrically neutral. Furthermore, since the charged droplets are repelled one from another, there is little or no coalescing of the droplets. On the contrary, the charged droplets tend to spread out to a great extent as compared to uncharged droplets. In addition if the repulsive forces from the charge within the droplets is greater than the surface tension force of the droplets, the charged droplets are caused to fragment into a plurality of smaller charged droplets (exceeding the Rayleigh limit). This process continues until either the two opposing forces are equalised or the droplet has fully evaporated.

Malodour particles are normally electrically isolated from their surroundings and will typically be at a potential which is the same as that of their surroundings. In this situation, a malodour particle located within a cloud of electrically charged liquid droplets thus is likely to cause a distortion in the configuration of the electrical field generated by the droplets so that the attraction of the droplets onto the particle will be improved. This amounts to the targeting of each malodour particle.

Examples of malodour counteractants which may be used in the method according to the present invention are those forming all or a part of the following currently available products: Arbor Vitae, benzyl salicylate, chlorophyll, cyclodextrins, d-limonene, flavanoids, Hinoki oil, parsley extract, phthalo-cyanine, saponin, tea tree oil, Tego Sorb (T. H. Goldschmidt), Veilex I, II or III (Bush Boake Allen) and the two aldehyde system described in U.S. Pat. No. 5,795,566.

The liquid composition which is sprayed into the air using the aerosol spray device is preferably a water and hydrocarbon mixture, or emulsion, or a liquid which is converted into an emulsion by shaking the spraying device before use, or during the spraying process. An example of a domestic aerosol composition which is in a form suitable for spraying in accordance with the method the invention is given in the Examples below.

Whilst all liquid aerosols are known to carry a net negative or positive charge as a result of double layer charging, or the fragmentation of liquid droplets, the charge imparted to droplets of liquid sprayed from standard devices is only of the order of $+/-1\times10^{-8}$ to $1\times10^{-5}$ C/kg.

The invention relies on combining various characteristics of the design of an aerosol spray system so as to increase the charging of the liquid as it is sprayed from the aerosol spray device.

A typical aerosol spray device comprises:
1. An aerosol can containing the composition to be sprayed from the device and a liquid or gaseous propellant;
2. A dip tube extending into the can, the upper end of the dip tube being connected to a valve;
3. An actuator situated above the valve which is capable of being depressed in order to operate the valve; and
4. An insert provided in the actuator comprising an orifice, from which the composition is sprayed.

A preferred aerosol spray device for use in the present invention is that described in WO97/12221.

It is possible to impart higher charges to the liquid droplets by choosing aspects of the aerosol device including the material, shape and dimensions of the actuator, the actuator insert, the valve and the dip tube and the characteristics of the liquid which is to be sprayed, so that the required level of charge is generated as the liquid is dispersed as droplets.

A number of characteristics of the aerosol system increase double layer charging and charge exchange between the liquid formulation and the surfaces of the aerosol system. Such increases are brought about by factors which may increase the turbulence of the flow through the system, and increase the frequency and velocity of contact between the liquid and the internal surfaces of the container and valve and actuator system.

By way of example, characteristics of the actuator can be optimised to increase the charge levels on the liquid sprayed from the container. A smaller orifice in the actuator insert, of a size of 0.45 mm or less, increases the charge levels of the liquid sprayed through the actuator. The choice of material for the actuator can also increase the charge levels on the liquid sprayed from the device with material such as nylon, polyester, acetal, PVC and polypropylene tending to increase the charge levels.

The geometry of the orifice in the insert can be optimised to increase the charge levels on the liquid as it is sprayed through the actuator. Inserts which promote the mechanical break-up of the liquid give better charging.

The actuator insert of the spray device may be formed from a conducting, insulating, semi-conducting or static-dissipative material.

The characteristics of the dip tube can be optimised to increase charge levels in the liquid sprayed from the container. A narrow dip tube, of for example about 1.27 mm internal diameter, increases the charge levels on the liquid, and the dip tube material can also be changed to increase charge.

Valve characteristics can be selected which increase the charge to mass ratio of the liquid product as it is sprayed from the container. A small tailpiece orifice in the housing, of about 0.65 mm, increases product charge to mass ratio during spraying. A reduced number of holes in the stem, for example 2×0.50 mm, also increases product charge during spray. The presence of a vapour phase tap helps to maximise the charge levels, a larger orifice vapour phase tap of, for example, about 0.50 mm to 1.0 mm generally giving higher charge levels.

Changes in the product formulation can also affect charging levels. A formulation containing a mixture of hydrocarbon and water, or an emulsion of an immiscible hydrocarbon and water, will carry a higher charge to mass ratio when sprayed from the aerosol device than either a water alone or hydrocarbon alone formulation.

It is preferred that a malodour counteracting. composition of use in the present invention comprises an oil phase, an aqueous phase, a surfactant, a malodour counteractant and a propellant.

Preferably the oil phase includes a $C_9$–$C_{12}$ hydrocarbon which is preferably present in the composition in the amount of from 2 to 10% w/w.

Preferably the surfactant is glyceryl oleate or a polyglycerol oleate, preferably present in the composition in an amount of from 0.1 to 1.0% W/W.

Preferably the propellant is liquified petroleum gas (LPG) which is preferably butane, optionally in admixture with propane. The propellant may be present in an amount of from 10 to 90% w/w depending upon whether the composition is intended for spraying as a "wet" or as a "dry" composition. For a "wet" composition, the propellant is preferably present in an amount of from 20 to 50% w/w, more preferably in an amount of from 30 to 40% w/w.

The liquid droplets sprayed from the aerosol spray device will generally have a diameter in the range of from 5 to 100 micrometres with a peak of droplets of about 40 micrometres. The liquid which is sprayed from the aerosol spray device may contain a predetermined amount of a particulate material, for example, fumed silica, or a predetermined amount of a volatile sold material, such as menthol or naphthalene.

The method of the present invention during the counteraction of malodour, also accelerates the natural process of precipitation of airborne particles by indirect charging of the particles, thereby enabling the air quality to be improved quickly and conveniently.

Examples of malodours which may be counteracted, neutralised or reduced by the method of the present invention include tobacco smoke and vehicle exhaust fumes.

A can for an aerosol spray device according to the invention is formed of aluminium or lacquered or unlacquered tin plate or the like. The actuator insert of such an aerosol spraying device may be formed of, for instance, acetal resin. The valve stem lateral opening of such a device as preferably in the form of two apertures of diameter 0.51 mm.

The present invention will now be described, by way of examples only, with reference to the drawings.

Figure 2:
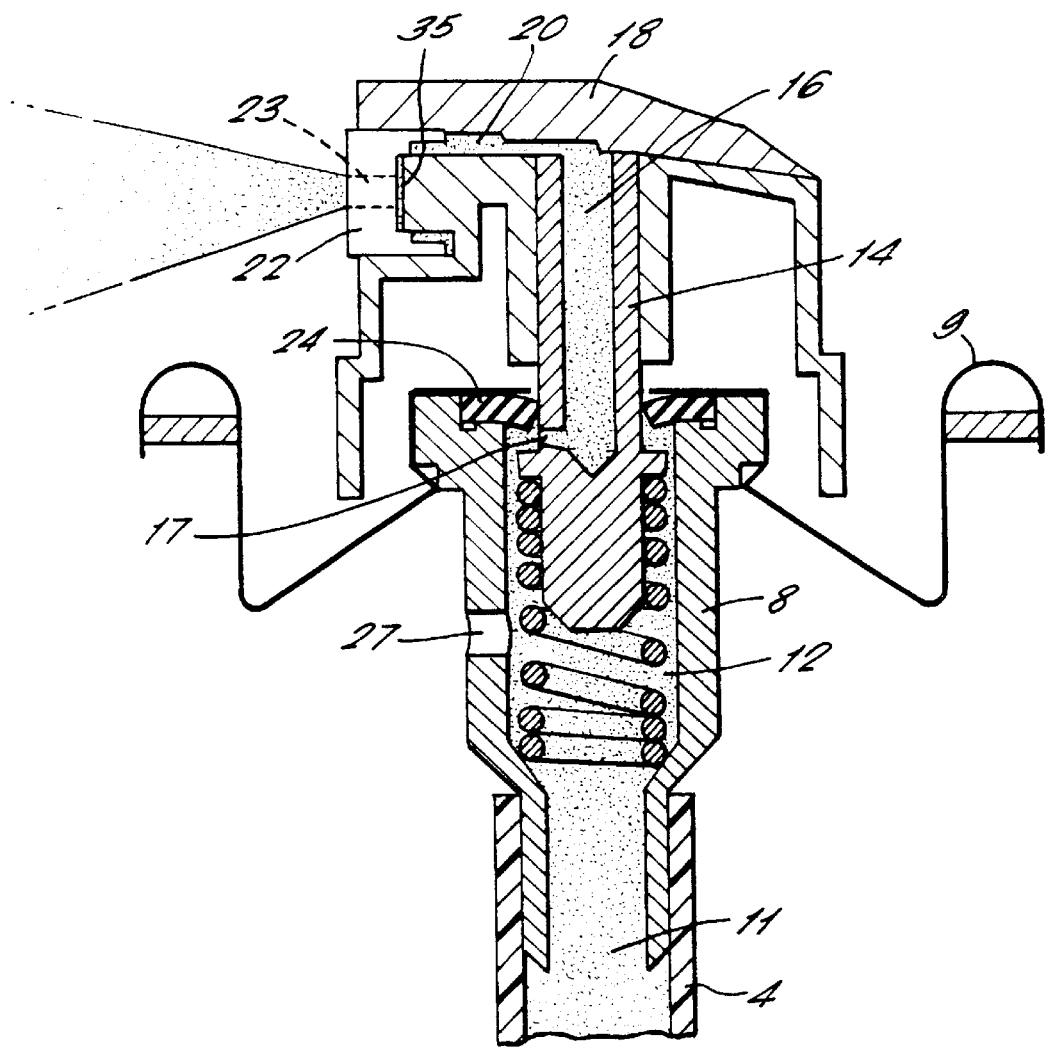
FIG. 2 is a diagrammatic cross section through the valve assembly of the apparatus of FIG. 1.
Figure 3:
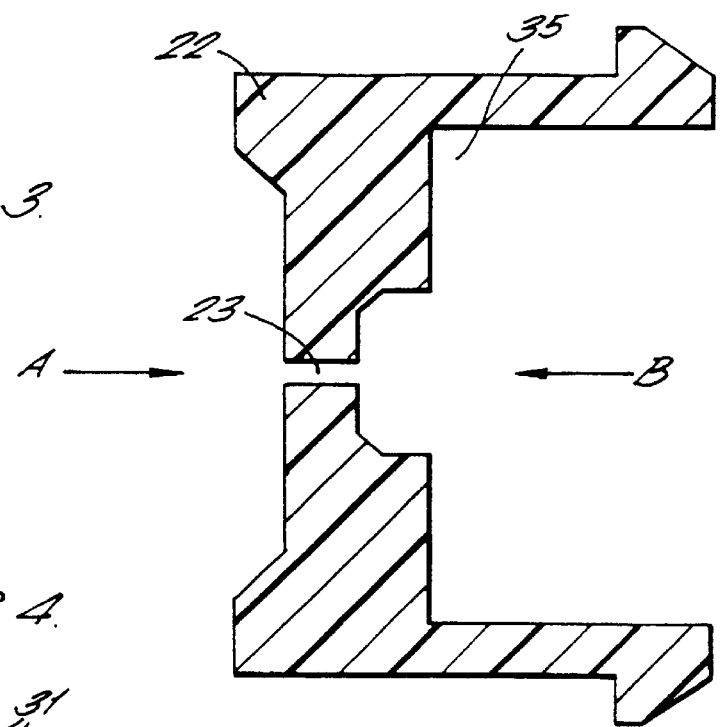
FIG. 3 is a cross section through the actuator insert of the assembly shown in FIG. 2.

Referring to FIGS. 1 and 2, an aerosol spray device in accordance with the invention is shown. It comprises a can 1, formed of aluminium or lacquered or unlacquered tin plate or the like in conventional manner, defining a reservoir 2 for a liquid 3 having a conductivity such that droplets of the liquid can carry an appropriate electrostatic charge. Also located in the can is a gas under pressure which is capable of forcing the liquid 3 out of the can 1 via a conduit system comprising a dip tube 4 and a valve and actuator assembly 5. The dip tube 4 includes one end 6 which terminates at a bottom peripheral part of the can 1 and another end 7 which is connected to a tailpiece 8 of the valve assembly. The tailpiece 8 is secured by a mounting assembly 9 fitted in an opening in the top of the can and includes a lower portion 10 defining a tailpiece orifice 11 to which end 7 of the dip tube 4 is connected. The tailpiece includes a bore 12 of relatively narrow diameter at lower portion 11 and a relatively wider diameter at its upper portion 13. The valve assembly also includes a stem pipe 14 mounted within the bore 12 of the tailpiece and arranged to be axially displaced within the bore 12 against the action of spring 15. The valve stem 14 includes an internal bore 16 having one or more lateral openings (stem holes) 17 (see FIG. 2). The valve assembly includes an actuator 18 having a central bore 19 which accommodates the valve stem 14 such that the bore 16 of the stem pipe 14 is in communication with bore 19 of the actuator. A passage 20 in the actuator extending perpendicularly to the bore 19 links the bore 19 with a recess including a post 21 on which is mounted a spraying head in the form of an insert 22 including a bore 23 which is in communication with the passage 20.

A ring 24 of elastomeric material is provided between the outer surface of the valve stem 14 and, ordinarily, this sealing ring closes the lateral opening 17 in the valve stem 14. The construction of the valve assembly is such that when the actuator 18 is manually depressed, it urges the valve stem 14 downwards against the action of the spring 15 as shown in FIG. 2 so that the sealing ring 24 no longer closes the lateral opening 17. In this position, a path is provided from the reservoir 2 to the bore 23 of the spraying head so that liquid can be forced, under the pressure of the gas in the can, to the spraying head via a conduit system comprising the dip tube 4, the tailpiece bore 12, the valve stem bore 16, the actuator bore 19 and the passage 20.

An orifice 27 (not shown in FIG. 1) is provided in the wall of the tailpiece 8 and constitutes a vapour phase tap whereby the gas pressure in the reservoir 2 can act directly on the liquid flowing through the valve assembly. This increases the turbulence of the liquid. It has been found that an increased charge is provided if the diameter of the orifice 27 is at least 0.76 mm.

Preferably the lateral opening 17 linking the valve stem bore 16 to the tailpiece bore 12 is in the form of two orifices each having a diameter of not more than 0.51 mm to enhance electrostatic charge generation. Further, the diameter of the dip tube 4 is preferably as small as possible, for example, 1.2 mm, in order to increase the charge imparted to the liquid. Also, charge generation is enhanced if the diameter of the tailpiece orifice 11 is as small as possible eg not more than about 0.64 mm.

Figure 4:
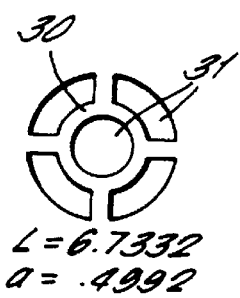
FIG. 4 shows the configuration of the bore of the spraying head shown in FIG. 3 when viewed in the direction A.
Figure 5:
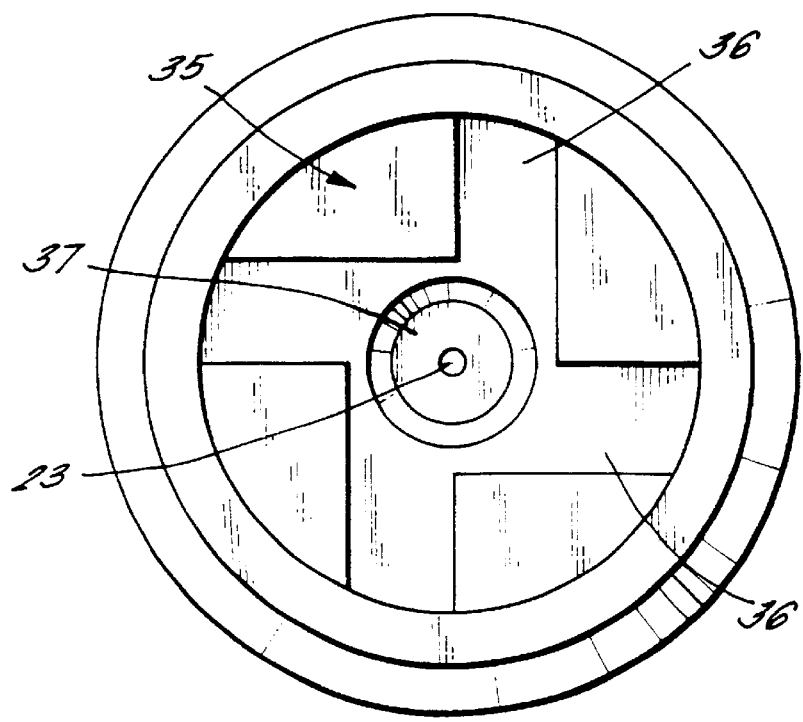
FIG. 5 shows the configuration of the swirl chamber of the spraying head shown in FIG. 3 when viewed in the direction B.

Referring now to FIG. 3, there is shown on an increased scale, a cross section through the actuator insert of the apparatus of FIGS. 1 and 2. For simplicity, the bore 23 is shown as a single cylindrical aperture in this Figure. However, the bore 23 preferably has the configuration, for instance, shown in FIG. 4. The apertures of the bore 23 are denoted by reference numeral 31 and the aperture-defining portions of the bore are denoted by reference numeral 30. The total peripheral length of the aperture-defining portions at the bore outlet is denoted by L (in mm) and a̲ is the total area of the aperture at the bore outlet (in $mm^2$) and the values for L and a̲ are as indicated in FIG. 4. L/a̲ exceeds 8 and this condition has been found to be particularly conductive to charge development because it signifies an increased contact area between the actuator insert and the liquid passing there through.

Many different configurations can be adopted in order to produce a high L/a̲ ratio without the cross-sectional area a being reduced to a value which would allow only low liquid flow rates. Thus, for example it is possible to use actuator insert bore configurations (i) wherein the bore outlet comprises a plurality of segment-like apertures (with or without a central aperture); (ii) wherein the outlet comprises a plurality of sector-like apertures; (iii) wherein the aperture together form an outlet in the form of a grill or grid; (iv) wherein the outlet is generally cruciform; (v) wherein the apertures together define an outlet in the form of concentric rings; and combinations of these configurations. Particularly preferred are actuator insert bore configurations wherein a tongue like portion protrudes into the liquid flow stream and can be vibrated thereby. This vibrational property may cause turbulent flow and enhanced electrostatic charge separation of the double layer, allowing more charge to move into the bulk of the liquid.

Referring now to FIG. 5, there is shown a plan view of one possible configuration of swirl chamber 35 of the actuator insert 22. The swirl chamber includes four lateral channels 36 equally spaced and tangential to a central area 37 surrounding the bore 23. In use, the liquid driven from the reservoir 2 by the gas under pressure travels along passage 20 and strikes the channels 36 normal to the longitudinal axis of the channels. The arrangement of the channels is such that the liquid tends to follow a circular motion prior to entering the central area 37 and thence the bore 23. As a consequence, the liquid is subjected to substantial turbulence which enhances the electrostatic charge in the liquid.

The following Examples illustrate the invention:

EXAMPLE 1

An air freshener fornulation was produced as follows:

83% by weight of an isoparaffin solvent was introduced into a mixing vessel and stirred. 0.2% by weight of butyl hydroxy toluene was added to the vessel as a corrosion inhibitor and stirring was continued until a homogeneous mixture was obtained. Thereafter, in turn, 5% by weight of polyglycerol oleate emulsifier and 11.8% by weight of a malodour counteractant/neutraliser were added and stirring was again continued until a homogenous mixture had been produced. This mixture constituted the oil phase of the final product. 6% by weight of this oil phase was placed in a tin plated aerosol can of the type described in connection with FIGS. 1 and 2 and having a spraying head bore configuration as shown in FIG. 4 and a spraying head swirl chamber configuration as shown in FIG. 5. The actuator insert was formed of acetal resin. The Malve stem lateral opening 17 was in the form of two apertures of diameter 0.51 mm, the vapour phase tap orifice 27 had a diameter of 0.76 mm, the tail pipe orifice 11 had a diameter of 0.64 mm and the diameter of the dip tube 4 was 3 mm. 59% by weight of soft water was then added to the can and thereafter the valve assembly was fitted onto the can. 35% by weight of butane was introduced into the can via the valve assembly to achieve a pressure of 40 psi within the can.

On depression of the actuator 18, a fine spray of liquid droplets having a charge/mass ratio of $-1\times10^{-4}$ C/kg and a flow rate of approximately 1.5 g/sec was obtained. The droplets became rapidly dispersed in the air.

The above-described aerosol spray device was compared with a standard, known aerosol spray device loaded with the same aerosol formulation in the following test.

Smoke Malodour Counteractancy Test

The experiment was panel based. In order to be able to assess the results, it was necessary to measure the threshold levels of the panellists. By choosing panellists of the same threshold value, a more accurate result could be obtained.

Threshold Testing

6 Samples of fragrance with diethyl phthalate (DEP) were made up at different fragrance concentrations. They were placed in amber, wide necked glass jars and labelled as follows:

A=2% solution, 0.6 g fragrance diluted with 29.4 g DEP

B=0.5% solution, 0.15 g fragrance diluted with 29.85 g DEP

C=0.05% solution, 0.015 g fragrance diluted with 29.985 g DEP

D=0.005% solution, 0.0015 g fragrance diluted with 29.9985 g DEP

E=0.0005% solution, 0.00015 g fragrance diluted with 29.99985 g DEP

F=Standard, 30 g DEP

G=Standard, 30 g DEP

A group of prospective panellists were then asked to pick "the odd one out" using F+G as the standard samples all the time and any one of the other samples. Starting at the strongest, (A), they were asked three times to pick out the samples they suspected to be fragranced.

The panellists who achieved consistent correctly answers for fragrances in the ranges A–C were chosen as final panellists for the following experiment. It should be noted that none of the panellists were able to predict fragrance D with 100% certainty.

The testing was carried out using three booths of controlled temperature and humidity. Into all booths, cigarette smoke was introduced through the artificial smoking of two Marlboro cigarettes. After this the booths were treated as below:

Booth 1

0.5 g of a normal aerosol spray was sprayed into the centre of the booth.

Booth 2

Into this booth 0.5 g of an electrostatically charged aerosol spray was introduced into the centre of the booth.

Booth 3

This was left with just the tobacco smoke added in order for the panellists to refresh themselves of the reference malodour, as appropriate.

Fifteen panellists were asked to choose which booth from booths 1 or 2 had the strongest tobacco malodour as referred to in booth 3. The results were statistically interpreted to establish significance which showed that the electrostatically charged spray in booth 2 significantly reduced the perceived malodour as compared to the normal aerosol spray in booth 1.

Further examples of malodour counteracting compositions will now be given, that can be formulated according to the method of Example 1 above.

EXAMPLE 2

| Component | % w/w |
|---|---|
| Butane 40 propellant | 35 |
| $C_9$—$C_{12}$ Hydrocarbon | 5.0 |
| Polyglycerol Oleate | 0.30 |
| Butylated Hydroxy Toluene | 0.0130 |
| Diethylphthlate | 0.70 |
| Arbor Vitae | 0.2 |
| Soft Water | to make up to 100% |

EXAMPLE 3

| Component | % w/w |
|---|---|
| Butane 40 propellant | 35 |
| $C_9$—$C_{12}$ Hydrocarbon | 5.0 |
| Polyglycerol Oleate | 0.30 |
| Butylated Hydroxy Toluene | 0.0130 |
| Diethylphthlate | 0.70 |
| Benzyl Salicate | 0.2 |
| Soft Water | to make up to 100% |

EXAMPLE 4

| Component | % w/w |
|---|---|
| Butane 40 propellant | 35 |
| $C_9$—$C_{12}$ Hydrocarbon | 5.0 |
| Polyglycerol Oleate | 0.30 |
| Butylated Hydroxy Toluene | 0.0130 |
| Diethylphthlate | 0.70 |
| Carra Scent | 0.2 |
| Soft Water | to make up to 100% |

One or more of the following malodour counteractants, may be used in compositions of Example 1 to 4, in place of the malodour counteractant of these Examples

| | | |
|---|---|---|
| Arbor Vitae | parsley extract | Veilex I, II or |
| benzyl salicylate | phthalocyanine | III (from Bush |
| chlorophyll | saponin | Boake Allen) and |

-continued

| | | |
|---|---|---|
| cyclodextrins | tea tree oil | the two aldehyde |
| d-limonene | Tego Sorb | system described |
| flavanoids | | in U.S. Pat. No. |
| Hinoki oil | | 5795566. |

What is claimed is:

1. A method of counteracting or neutralising airborne malodour comprising directing at the source of the malodour liquid droplets from a spray device containing a malodour counteracting composition, a unipolar charge being imparted to the liquid droplets by double layer charging during the spraying of the liquid droplets by the spray device, the unipolar charge being at a level such that said droplets have a charge to mass ratio of at least $\pm 1 \times 10^{-4}$ C/kg.

2. A method as claimed in claim 1 wherein the spray device is an aerosol spray device.

3. A method as claimed in claim 2 wherein the malodour counteracting composition is an emulsion.

4. A method as claimed in claim 3 wherein the liquid droplets have a diameter in the range of from 5 to 100 micrometres.

5. A method as claimed in claim 4 wherein the composition includes a malodour counteractant selected from one or more of Arbor Vitae, benzyl salicylate, chlorophyll, cyclodextrins, d-limonene, flavanoids, Hinoki oil, parsley extract, phthalocyanine, saponin, tea tree oil or Tego Sorb.

6. A method as claimed in claim 4 wherein the unipolar charge is imparted to the liquid droplets solely by the interaction between the liquid and the spray device, without any charge being imparted thereto from an internal or external charge inducing device.

7. A method as claimed in claim 6 wherein the required droplet charge to mass ratio is imparted to the liquid droplets as a result of the use of an aerosol spray device with at least one of the features of:

(a) the material of the actuator,
(b) the size and shape of the orifice of the actuator,
(c) the diameter of the dip tube,
(d) the characteristics of the valve, and
(e) the formulation of the malodour counteracting composition contained within the aerosol device being chosen in order to achieve said droplet charge to mass ratio by double layer charging imparting the unipolar charge to the droplets during the actual spraying of the liquid droplets from the orifice of the aerosol spray device.

8. A method as claimed in claim 7 wherein the malodour counteracting composition comprises an oil phase, an aqueous phase, a surfactant, a malodour counteractant and a propellant.

9. A method as claimed in claim 8 wherein the oil phase includes a $C_9$–$C_{12}$ hydrocarbon.

10. A method as claimed in claim 9 wherein the $C_9$–$C_{12}$ hydrocarbon is present in the composition in an amount of from 2 to 10% w/w.

11. A method as claimed in claim 8 wherein the surfactant is glyceryl oleate or a polyglycerol oleate.

12. A method as claimed in claim 11 wherein the surfactant is present in the composition in an amount of from 0.1 to 1.0% w/w.

13. A method as claimed in claim 8 wherein the propellant is liquified petroleum gas.

14. A method as claimed in claim 13 wherein the propellant is present in tile composition in an amount of from 20 to 50% w/w.

* * * * *